United States Patent
Kollgaard et al.

(10) Patent No.: US 7,553,070 B2
(45) Date of Patent: Jun. 30, 2009

(54) INFRARED NDI FOR DETECTING SHALLOW IRREGULARITIES

(75) Inventors: Jeffrey R. Kollgaard, Kent, WA (US); Jeffrey G. Thompson, Kent, WA (US); Clyde T. Uyehara, Kent, WA (US)

(73) Assignee: The Boeing Company, Chicago, IL (US)

( * ) Notice: Subject to any disclaimer, the term of this patent is extended or adjusted under 35 U.S.C. 154(b) by 175 days.

(21) Appl. No.: 11/556,723

(22) Filed: Nov. 6, 2006

(65) Prior Publication Data
US 2008/0107147 A1 May 8, 2008

(51) Int. Cl.
*G01N 25/18* (2006.01)
*G01N 25/72* (2006.01)

(52) U.S. Cl. .............. 374/5; 374/30; 374/112; 250/341.1; 250/341.6

(58) Field of Classification Search ............ 374/4, 374/5, 10, 11, 30, 57, 110, 112, 121, 124, 374/132, 166–167, 208, E3.006, E3.009, 374/E1.019; 356/237.2; 73/583; 244/126; 250/341.1, 341.6, 349
See application file for complete search history.

(56) References Cited

U.S. PATENT DOCUMENTS

| | | | | |
|---|---|---|---|---|
| 3,451,254 | A | * | 6/1969 | Maley .............. 374/5 |
| 3,462,602 | A | * | 8/1969 | Apple ............. 250/338.1 |
| 3,813,926 | A | | 6/1974 | Stubbeman |
| 3,854,336 | A | * | 12/1974 | Bibby ............. 374/124 |
| 4,215,583 | A | | 8/1980 | Botsco et al. |
| 4,435,092 | A | * | 3/1984 | Iuchi ............... 374/129 |
| 4,840,066 | A | | 6/1989 | Botsco et al. |
| 4,866,276 | A | * | 9/1989 | Leavens et al. ......... 250/341.6 |
| 4,879,796 | A | | 11/1989 | Nakamura et al. |
| 5,163,027 | A | | 11/1992 | Miller et al. |
| 5,165,796 | A | * | 11/1992 | Gat et al. ............. 374/128 |
| 5,376,793 | A | * | 12/1994 | Lesniak .............. 250/341.6 |
| 5,433,106 | A | | 7/1995 | Matsumura et al. |

(Continued)

FOREIGN PATENT DOCUMENTS

DE 34 07 911 A1 9/1985

(Continued)

OTHER PUBLICATIONS

Imaeva, L.A., et al., "Ultrasound Inspection of Multilayered Cellular Structures Produced By Superplastic Forming and Diffusion Bonding", vol. 15, No. 11, 2001, pp. 895-897.

(Continued)

*Primary Examiner*—Patrick J Assouad
*Assistant Examiner*—Bret Adams
(74) *Attorney, Agent, or Firm*—Alston & Bird LLP

(57) ABSTRACT

First and second thermal sensors measure the respective temperatures of portions of a surface of a structure such as an aircraft component. An alert signal is emitted if the temperatures of the surface portions are substantially different. An energy source causes heat flow within the structure. Subsurface irregularities such as disbanded areas between composite layers and foreign materials obstruct heat flow within the structure and cause proximate surface portions to exhibit different temperatures. A non-alert signal may be emitted if the temperatures of proximate surface portions are essentially the same.

23 Claims, 4 Drawing Sheets

U.S. PATENT DOCUMENTS

| | | | |
|---|---|---|---|
| 5,582,485 A * | 12/1996 | Lesniak | 374/5 |
| 5,618,994 A | 4/1997 | Falsetti | |
| 5,646,406 A * | 7/1997 | Sporck et al. | 250/342 |
| 5,963,662 A * | 10/1999 | Vachtsevanos et al. | 382/150 |
| 6,000,844 A * | 12/1999 | Cramer et al. | 374/5 |
| 6,073,477 A | 6/2000 | Woodmansee et al. | |
| 6,346,704 B2 * | 2/2002 | Kenway | 250/341.6 |
| 6,690,016 B1 * | 2/2004 | Watkins et al. | 250/341.7 |
| 6,712,502 B2 * | 3/2004 | Zalameda et al. | 374/5 |
| 6,751,342 B2 * | 6/2004 | Shepard | 382/141 |
| 6,860,634 B2 * | 3/2005 | Shigeoka | 374/131 |
| 6,874,932 B2 * | 4/2005 | Devitt et al. | 374/5 |
| 7,048,756 B2 * | 5/2006 | Eggers et al. | 607/113 |
| 7,070,325 B2 * | 7/2006 | Heerdt et al. | 374/129 |
| 2002/0151817 A1 * | 10/2002 | Gentempo et al. | 600/549 |
| 2004/0262521 A1 | 12/2004 | Devitt | |
| 2005/0263646 A1 | 12/2005 | Nichols | |
| 2005/0279171 A1 * | 12/2005 | Kollgaard et al. | 73/627 |
| 2006/0029121 A1 | 2/2006 | Boehmisch | |
| 2006/0043303 A1 * | 3/2006 | Safai et al. | 250/347 |
| 2006/0124853 A1 | 6/2006 | Witthoft | |
| 2006/0191622 A1 | 8/2006 | Ritter | |
| 2007/0084290 A1 * | 4/2007 | Fetzer et al. | 73/627 |

FOREIGN PATENT DOCUMENTS

| | | |
|---|---|---|
| DE | 299 08 615 U1 | 6/2000 |
| GB | 2 164 147 A | 3/1986 |
| GB | 2 168 494 A | 6/1986 |

OTHER PUBLICATIONS

PCT/US2007,021753, International Search Report dated Jun. 2, 2008.

* cited by examiner

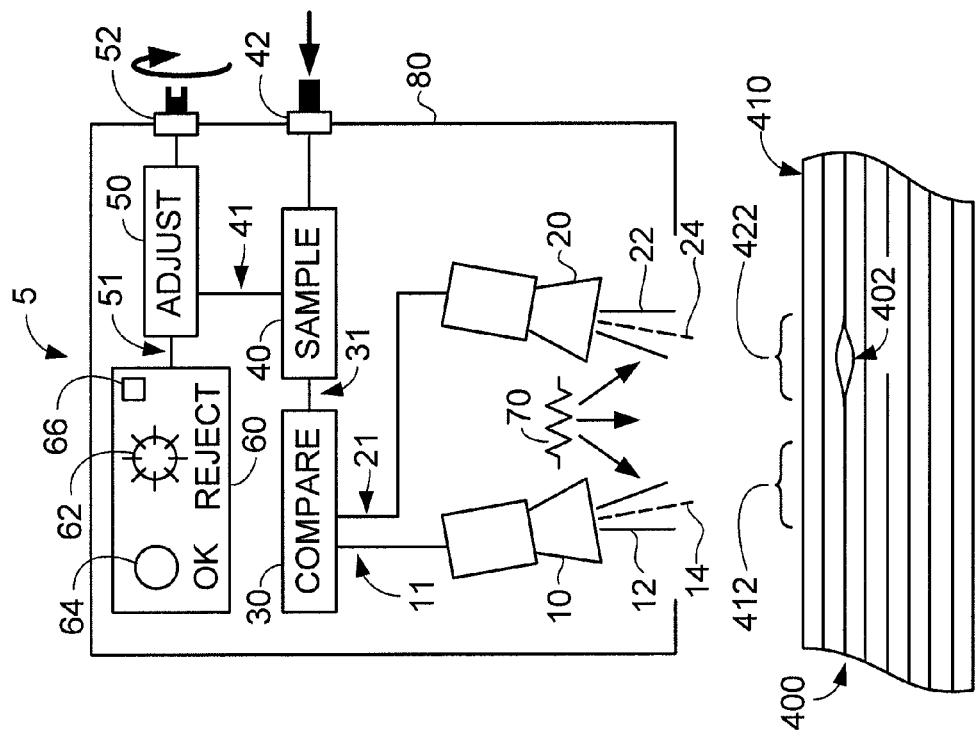
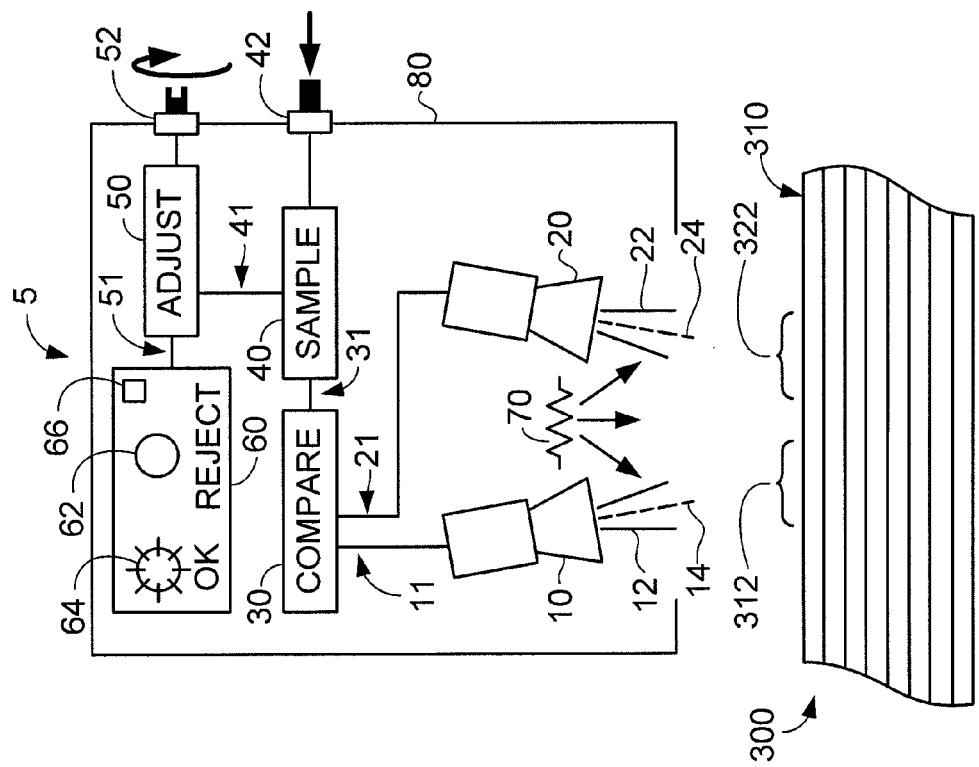

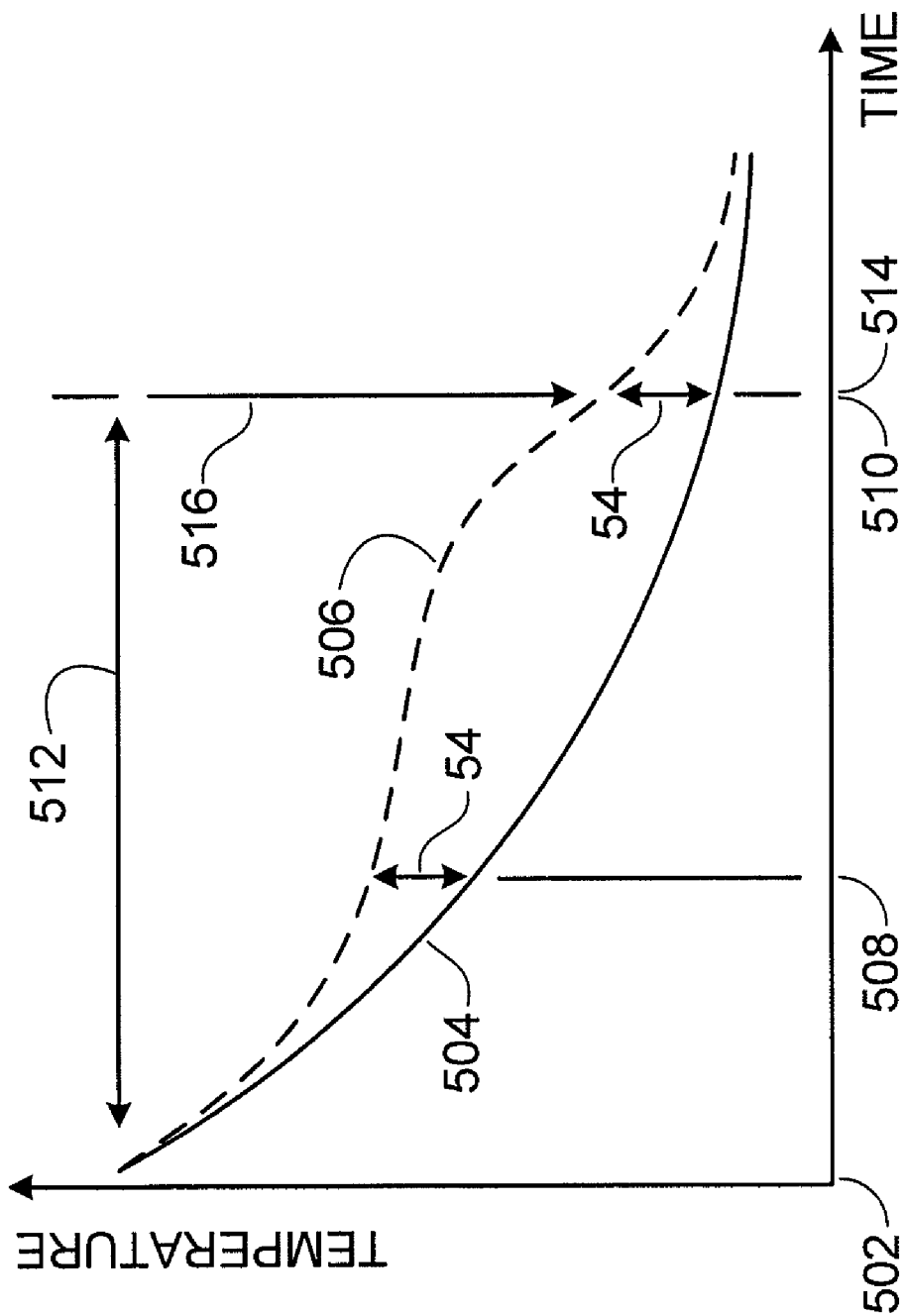

US 7,553,070 B2

INFRARED NDI FOR DETECTING SHALLOW IRREGULARITIES

TECHNICAL FIELD

Embodiments of the present disclosure relate generally to non-destructive devices and methods for inspecting structures. More particularly, embodiments of the disclosure relate to devices and methods for inspecting a skin of a structure for the presence of shallow sub-surface irregularities, damages, and trapped foreign matter.

BACKGROUND

Non-destructive inspection (NDI) of structures involves examining a structure without harming the structure or requiring significant disassembly. NDI methods are often preferred in order to avoid the time and costs associated with the removal of a part and to avoid the potential for causing damages when inspection is needed. In some situations, NDI methods might be the only methods by which inspections may be performed. NDI devices and methods are used in the aircraft industry to inspect aircraft structures such as composite structures and bonded panels. Inspections may identify irregularities such as cracks, discontinuities, disbonds between layers, voids, and areas having undesirable porosity. Preventive inspections may be performed during manufacturing and at any time during the service life of an aircraft structure to confirm the integrity and fitness of the structure. Inspections may also be prompted by incidents such as collisions and ballistic impacts.

NDI methods that include infrared imaging are available but involve costly equipment and a high degree of training. For example, infrared imaging, or thermography, is used in aircraft industries to inspect composite honeycomb parts for the presence of moisture ingression and to inspect fuselage components for disbonds between layered composite materials. In these applications, infrared imaging provides a graphical display of an inspected structure. Such a display can reveal, to the trained eye, sub-surface irregularities in a structure. However, the necessary infrared cameras and technicians trained to interpret thermographic displays represent considerable costs. Thus, while the equipment and experience needed for infrared imaging may be available at specialized repair and maintenance facilities, they are not typically readily available at commercial airports and remote aviation facilities.

The skin of an aircraft can have many surface marks. Some surface marks are superficial and are of little or no importance. Other marks overlay undesirable sub-surface damage of the marked component. Crews that fuel, load, and generally prepare airplanes for flight face a critical challenge. However, needless grounding of planes out of concerns over minor bumps and scratches must be minimized to preserve the commercial viabilities of airline companies, in order to efficiently serve traveling customers, and in order for military aircraft to provide critical support to ground-deployed forces in situations where time may be of critical essence.

In many scenarios, maintenance crews would benefit from having devices and methods for inspecting component skins and repair patches for evidence of shallow damages and irregularities.

It would be advantageous to provide low-cost NDI devices for rapid screening of markings on aircraft-component skins to determine whether shallow sub-surface damages are present. It would be advantageous to provide NDI devices and methods that permit a ground crew, without extensive thermography training, to determine whether a scratched or marked aircraft structure is ready to fly or whether extensive inspections by specialized personnel and equipment are needed. A need exists for low-cost NDI devices that can be feasibly widely distributed at aviation facilities, and that can be used to make rapid fly versus no-fly decisions.

SUMMARY

Embodiments of the disclosure may address at least some of the above needs and achieve other advantages. A first aspect of the disclosure relates to a method of inspecting a structure. The method includes the steps of measuring the temperature of a first portion of a surface of a structure with a first thermal sensor, measuring the temperature of a second portion of the surface of the structure with a second thermal sensor, and emitting an alert signal if the temperature of the first portion is substantially different from the temperature of the second portion. For example, first and second thermal radiometers having respective fields of view may be used to measure the temperatures of the first and second portions of the surface. A non-alert signal may be emitted if the temperatures of the surface portions are essentially the same. In at least one embodiment of a method according to the disclosure, an area of the surface is heated, the area including the first and second portions.

A second aspect of the disclosure relates to an inspection device. An embodiment of the device includes a first radiometer, a second radiometer, an indicator element, and a comparator. The first and second radiometers have respective fields of view along different respective axes. Each radiometer is capable of generating a signal indicative of the temperature of a surface when a surface is disposed in its field of view. The comparator is capable of causing the indicator element to indicate whether the indicated temperatures are substantially different. The indicator element may include first and second indicators, in which case the comparator is capable of causing the first indicator to indicate when the temperatures are substantially different and causing the second indicator to indicate when the temperatures are not substantially different. The first and second indicators may include light emitters capable of emitting different colors of light. The device may include an energy source operable to cause heating of a structure.

A third aspect of the disclosure relates to a method of inspecting the skin of a structure below the surface of the skin. According to an embodiment of the method, a skin of a structure is heated through an outward surface of the skin to cause heating of the surface. Respective temperatures of proximate portions of the heated surface are concurrently measured using a proximate pair of infrared radiometers. The presence of an irregularity within the skin below the surface is determined by observing a difference in the respective temperatures. Heating the skin may entail directing thermal energy or ultrasonic energy onto the surface.

A fourth aspect of the disclosure relates to a method of inspecting an aircraft structure, which may include multiple layers of composite material. According to an embodiment of the disclosure, a surface of an aircraft structure is heated and a determination is made as to whether a temperature difference is present by concurrently measuring respective temperatures of proximate portions of the heated surface using a pair of thermal radiometers. The aircraft structure is returned to flying service if the temperatures are essentially the same, and further inspection is performed if the temperatures are substantially different. The surface may be visually inspected for impact sites. If an impact site is identified, the thermal radiometers are disposed near the impact site. The radiometers may be disposed at multiple locations near the impact site in order to determine whether temperature differences are present at each of the multiple locations.

BRIEF DESCRIPTION OF THE SEVERAL VIEWS OF THE DRAWINGS

Figure 2:
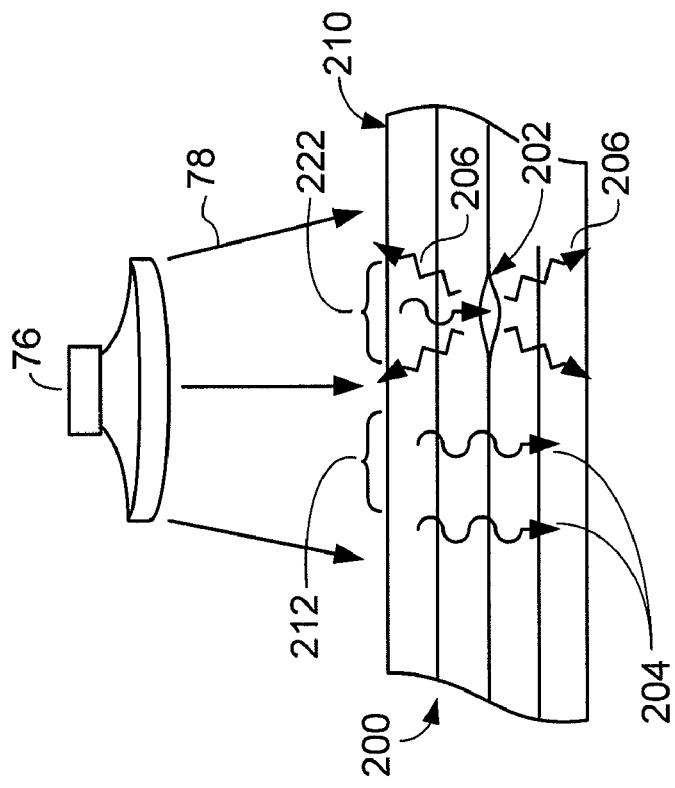
Figure 1:
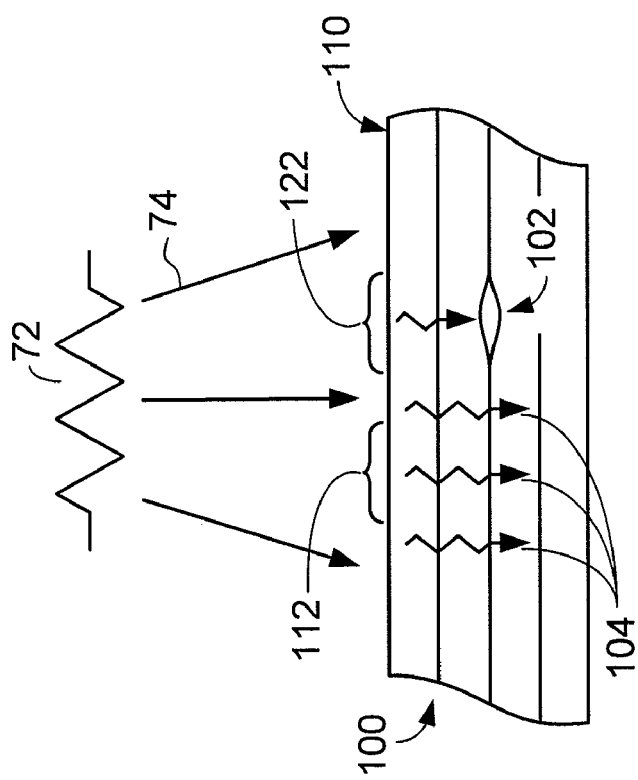
Figure 6:
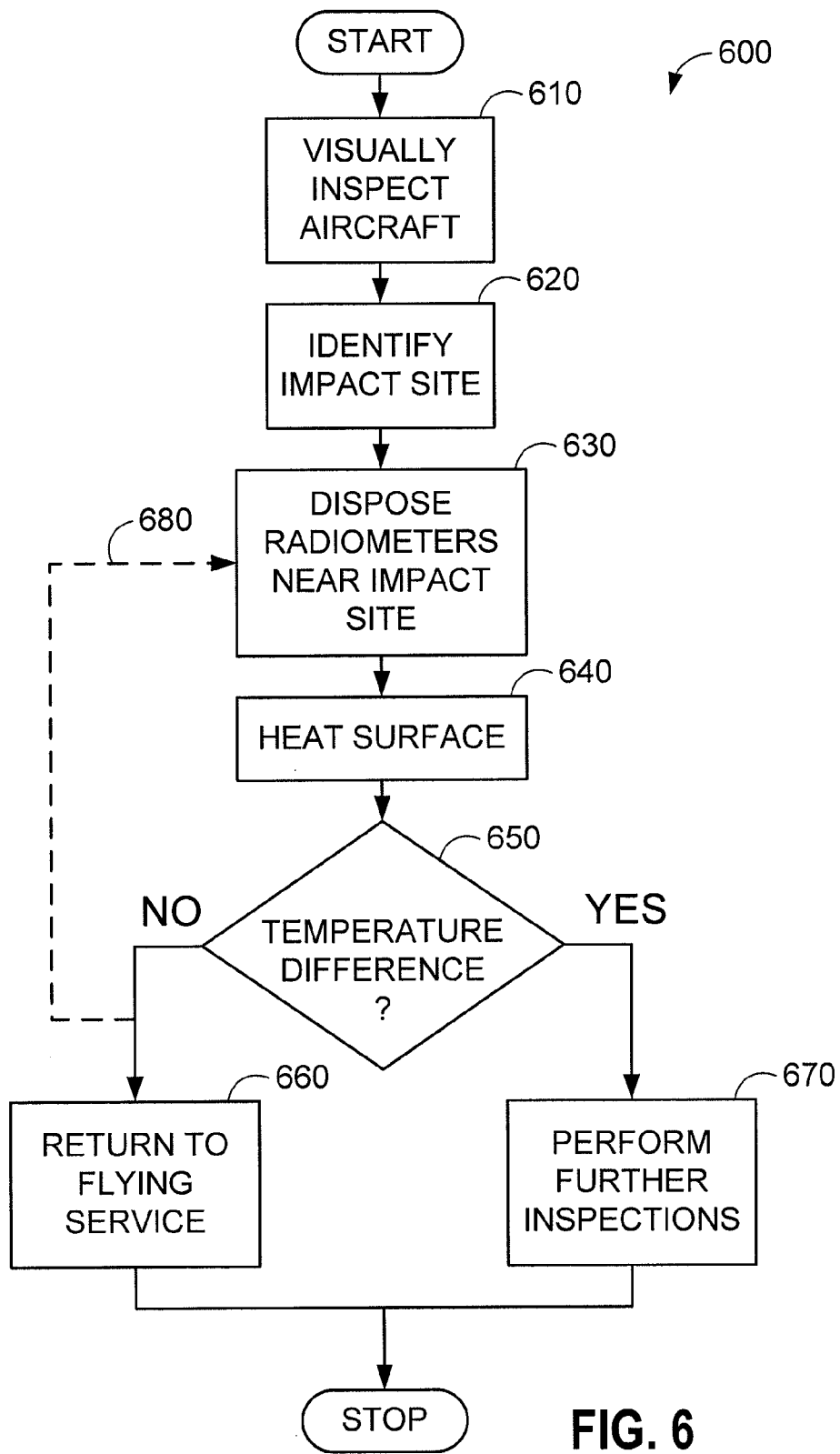

Having thus described the embodiments in general terms, reference will now be made to the accompanying drawings, which are not necessarily drawn to scale, and wherein:

FIG. 1 illustrates a theoretical approach to understanding how a radiant-heat device can cause an elevated surface temperature in the vicinity of a subsurface irregularity;

FIG. 2 illustrates a theoretical approach to understanding how an ultrasonic acoustic device can cause an elevated surface temperature in the vicinity of a subsurface irregularity;

FIG. 3 is a diagrammatic environmental view of an inspection device, in accordance with one embodiment of the present disclosure, deployed in an inspection scenario along the surface of a structure and emitting a non-alert signal indicating that no sub-surface irregularity are detected;

FIG. 4 is a diagrammatic environmental view of the inspection device of FIG. 3, deployed in an inspection scenario along the surface of a structure and emitting an alert signal indicating that a sub-surface irregularity may be present;

FIG. 5 is a simulated temperature-curve diagram charting the temperatures of surface portions of the structure in FIG. 4; and FIG. 6 is a flowchart representation of a method of inspecting an aircraft structure according to an embodiment of the present disclosure.

DETAILED DESCRIPTION OF THE INVENTION

One or more embodiments now will be described more fully hereinafter with reference to the accompanying drawings, in which some, but not all embodiments are shown. Indeed, the disclosure may be embodied in many different forms and should not be construed as limited to the embodiments set forth herein; rather, these embodiments are provided so that this disclosure will satisfy applicable legal requirements. Like numbers refer to like elements throughout.

A theoretical approach to understanding the flow of heat into a structure, the production of heat within a structure in response to incident energy such as ultrasonic energy, and the production of temperature gradients on the surface of a structure by which sub-surface irregularities may be detected are described herein with references to FIGS. 1-2. Such descriptions are provided to promote an understanding of concepts underlying the developments of various embodiments of the disclosure. Embodiments of the disclosure, however, are not bound or limited to any particular theoretical approach.

In FIGS. 1-2, energy sources cause heating of the surface of a structure such that temperature gradients along the surface can be observed and underlying sub-surface irregularities may be detected. In FIG. 1, an energy source 72 briefly and uniformly bathes a wide area of the surface 110 of a structure 100 with radiant thermal energy 74. Thermal energy 104 is conducted into the structure from the surface. A sub-surface irregularity 102 represents an irregularity in the structure that alters the heat conduction or heat capacity properties of the structure in the vicinity of the irregularity. Thus, as thermal energy 104 is conducted into the structure from the surface, the portion 122 of the surface overlying the irregularity is likely to temporarily exhibit a temperature that is different from that of the proximate surface portion 112.

For example, the sub-surface irregularity 102 can represent a void or a volume of high porosity. In this example, the irregularity 102 insulates against uniform heat flow across its vicinity and causes heat to be temporarily trapped near the surface 110. Thus, the surface portion 122 is expected to temporarily exhibit a higher temperature than that of the proximate surface portion 112. Ultimately, the trapped heat may flow laterally and around the irregularity 102 such that, once thermal equilibrium is established, the surface 110 may exhibit a uniform temperature across proximate portions 112 and 122. Nonetheless, a difference in temperature between the proximate surface portions 112 and 122 may temporarily provide evidence of the sub-surface irregularity 102.

For further example, the sub-surface irregularity can represent a contaminant having a relatively high heat capacity. For example the irregularity 102 can represent a bit of contaminant metal embedded in a layered composite structure. In this example, the surface portion 122 may temporarily exhibit a lowered temperature as the contaminant absorbs heat. Subsequently, as the thermal radiant energy 74 is stopped and the structure cools, the surface portion 122 may temporarily exhibit an elevated temperature as the contaminant releases heat. Thus, a sub-surface contaminant or irregularity may be detected by a raised or lowered surface temperature. In another example, the irregularity 102 can represent moisture ingression in a layered composite structure. The high heat capacity of water can cause temperature differences between moisture contaminated and moisture free portions of a structure. In this example, the surface portion 122 represents a portion of a skin over a honeycomb structure contaminated with water.

In FIG. 2, an energy source 76 briefly and uniformly bathes a wide area of the surface 210 of a structure 200 with ultrasonic energy 78. Ultrasonic energy 204 propagates into the structure from the surface. A sub-surface irregularity 202 represents an irregularity in the structure that alters the vibrational response of the structure in the vicinity of the irregularity. For example, the irregularity 202 can represent a disbonded area between adjacent layers in a composite structure. In this example, the heat of friction is generated by the vibrational response of the disbanded area to the propagating ultrasonic energy 204. This causes an elevated temperature in the structure at the irregularity and above the irregularity. Thus, the surface portion 222 overlying the sub-surface irregularity 202 may temporarily exhibit a temperature that is higher than that of the proximate surface portion 212.

Thus, if a surface of a structure is briefly bathed with energy that conveys or produces heat, sub-surface irregularities may be revealed by transient temperature gradients along the surface. The term "structure" is broadly used in these descriptions in referring to any physical member that has a front surface and a sub-surface composition that is expected to be laterally uniform along a distributed area of the surface. In that context, composition differences under proximate surface portions represent sub-surface irregularities. Sub-surface irregularities can include, but are not limited to: damages, contaminants; voids; cracks; porosity irregularities; repair artifacts; and other sub-surface conditions. An inspected structure can include any number of materials. An inspected structure can be a uniform and homogenous material, a layered material, a composite material such as graphite-epoxy, or combinations thereof.

However, in the interest of providing particular descriptions of inspection scenarios and embodiments of the present invention, the following descriptions refer to layered structures such as layered composite aircraft components like fuselage and wing members. Such an aircraft has an external skin that can be constructed of multiple layers of composite material. Nonetheless, the term "structure" as used herein relates to aircraft structures and other structures as well, including composite structures such as bridges and boats.

Furthermore, a structure can be layered upon its manufacture and can receive additional layers upon repair when a patch is bonded to the outer surface of a structure. Thus, an inspection can be related to assurance measures as a structure is manufactured and as repairs are made. For example, an operator can use the inspection device 5 illustrated in FIGS. 3-4 in attempting to determine whether a patch is properly bonded to the component. In particular, strips of backing material sometimes inadvertently remain on the adhesive side of a patch and become sandwiched between the patch and the component. In that context, the outer face of the patch defines a surface and the sandwiched backing material defines a sub-surface irregularity which may be detected by inspection along the surface of the patch. An inspection can additionally be related to determining whether surface markings overlay sub-surface irregularities.

An inspection device 5 according to an embodiment is illustrated in FIGS. 3-4. The inspection device includes a first thermal radiometer 10, a second thermal radiometer 20, a comparator 30 disposed in electronic communication with the first and second radiometers, a sample-and-hold circuit 40 disposed in electronic communication with the comparator, a level adjust device 50 disposed in electronic communication with the sample-and-hold circuit, and an indicator element 60 disposed in electronic communication with the level adjust device. The first radiometer 10 has a first field of view 12 along a first axis 14, and, the second radiometer 20 has a second field of view 22 along a second axis 24. A housing 80 maintains the relative dispositions of the radiometers such that the first axis is maintained as different from the second axis.

The first and second radiometers in FIGS. 3-4 comprise respective non-imaging radiometers, which are typically less expensive than thermal imaging devices such as infrared camera devices. Non-imaging radiometers generate signals that convey temperature information but not photographic information. Nonetheless, a non-imaging radiometer can be described as having a field of view, which is defined approximately as a cone having a diameter that increases monotonically with distance from the radiometer. When the field of view of a radiometer is directed toward a particular portion of a surface, the signal generated by the radiometer is indicative of the particular surface portion without regard to the temperatures of other portions of the surface. The field of view of a radiometer is typically specified as an aspect ratio that allows a determination of the approximate diameter of the field of view at any particular distance from the radiometer. For example, if a radiometer having a twelve-to-one aspect ratio is disposed twelve inches from a surface, the radiometer observes the temperature of a surface portion having a one inch diameter, approximately. A typical non-imaging radiometer generally receives infrared emissions, such as blackbody radiation, from an observed portion of a surface and generates a signal such as a DC voltage level that varies with the temperature of the observed surface portion. The first and second radiometers may be balanced devices having essentially identical response functions.

Furthermore, the first and second radiometers 10 and 20 comprise respective similar or essentially identical non-imaging radiometers having four-to-one aspect ratios. The inspection device 5 is disposed in FIG. 3 such that the radiometers are maintained approximately four inches from the surface 310. Thus, the fields of view 12 and 22 of the first and second radiometers are directed toward respective surface portions 312 and 322 having one inch diameters, approximately. The surface portions 312 and 322 respectively observed by the first and second radiometers 10 and 20 are proximate to each other, but are spaced apart by a distance measuring approximately one half of one inch. Furthermore, the first and second radiometers generate signals that vary approximately by ten millivolts per degree Celsius. Each provides an output that varies between zero and five volts across a temperature range between zero and five hundred degrees Celsius. Thus, the thermal radiometers 10 and 20 can be selected from commercially available devices. For example, such radiometers are available from Raytek®, a company which provides a variety of non-contact temperature measurement devices.

The comparator 30 receives the output signals 11 and 21 from the first and second radiometers and generates a difference signal 31 received by the sample and hold circuit 40. The difference signal of the comparator 30 conveys information regarding the difference, if any, between the temperatures measured by the first and second radiometers. The comparator may comprise transistor-transistor logic (TTL) circuits. The sample and hold circuit 40 receives the difference signal 31 of the comparator and generates a normalized difference signal 41. The sample and hold circuit 40 is prompted to initiate an inspection session when the trigger 42 is actuated by a user. When the trigger 42 is actuated, the sample and hold circuit samples the value of the difference signal 31 and nulls the normalized difference signal 41 in order to effectively balance the inspection device 5 with regard to the two radiometers at their current signal levels. Thus, minor drifts in the response functions of the two radiometers are nulled at the initiation of an inspection session. Subsequently, for the duration of the inspection session, as the device 5 is scanned over an inspection area, the normalized difference signal 41 conveys any departure of the difference signal 31 from its null value at the initiation of the session.

The level-adjust device 50 receives the normalized difference signal 41 and generates a signal 51 received by the indicator element 60. The level adjust device 50 controls the sensitivity of the inspection device 5, which may be used in various environments for inspecting various materials. For example, it is expected that inspections along the surface of the layered composite skin of an aircraft component may detect the presence of sub-surface irregularities by detecting temperature differences of two to six degrees Celsius. Such temperatures would translate to differences of twenty to sixty millivolts in the output signals of balanced radiometers having signals that vary approximately by ten millivolts per degree Celsius. Thus, in this example, a stable twenty millivolt difference between balanced output signals of such radiometers should ultimately alert an operator. However, a mere one millivolt difference may represent an insignificant temperature difference between proximate surface portions. Furthermore, a difference of a few millivolts may merely represent drifts in the response functions of the radiometers or a drift in the balancing of the signals. An adjustment device 52, such as a variable potentiometer or "turn pot" permits an operator of the inspection device or a calibration specialist to adjust the sensitivity of the inspection device by establishing a temperature difference threshold 54 (FIG. 5). In at least one embodiment, the adjustment device 52 is a concealed device disposed within the interior of the housing 80, and is accessible only by trained NDI specialists.

The indicator element 60 is illustrated to include a first indicator 62 and a second indicator 64. The first indicator 62 is activated when the temperatures indicated by the first and second radiometers are substantially different. Such a condition represents an alert signal that alerts the operator to the likelihood of a sub-surface irregularity in the vicinity of the current disposition of the inspection device 5. The second indicator 64 is activated when temperatures indicated by the first and second radiometers are essentially the same. Such a condition represents a non-alert signal that assures the operator that a sub-surface irregularity is not detected at the current disposition of the inspection device. The first and second indicators can comprise respective light sources such as LED devices. For example, the first indicator 62 can comprise an LED device that emits red light when activated, and the second indicator 64 can comprise an LED device that emits green light when activated. The indicator element 60 can additionally include an audible signal emitter 66 that emits an audible alarm as an additional alert signal when the first indicator 62 is activated.

An inspection device according to one or more embodiments of the disclosure may include, or be used in conjunction with, an energy source that is operable to cause heating of a structure under inspection. For example, the inspection device 5 of FIGS. 3-4 includes an energy source 70 that comprises a radiant-heat device having an electrically heated filament. The energy source 70 is operable to briefly and uniformly bathe a wide area of the surface 310 of the structure 300 with radiant thermal energy to cause heat to flow into the structure. The energy source is configured and disposed to bathe an area of the surface that includes the surface portions 312 and 322 and surrounding surface portions. The energy source 70 can be maintained within or connected to the housing 80, or can be provided as a separate device.

Other inspection devices according to other embodiments of the disclosure comprise other types of energy sources. For example, an inspection device according to at least one embodiment of the disclosure includes an energy source that comprises an ultrasonic acoustic device that excites heat production within an inspected structure as shown in FIG. 2. In general, an energy source causes thermal energy to flow through an inspected structure and out through the surface of the structure. An energy source, according to these descriptions, can include, but is not limited to: a radiant-heat device having an electrically heated filament; a radiant-heat device having an element heated by fuel-combustion or other exothermic reaction; an ultrasonic horn; a forced-air heat gun; a space heater; a flexible heating pad; a flash lamp; and even a volume of heated liquid splashed onto the structure under inspection. Furthermore, even sunlight and a human body portion such as a hand can be used as an energy source.

The particular inspection scenarios represented by FIGS. 3-4 are described in the following. In FIG. 3, the inspection device 5 is disposed near the surface 310 of a structure 300 to inspect the structure for sub-surface irregularities. The energy source 70 heats the structure through the surface and heat flows into and through the structure. The field of view 12 of the first radiometer 10 and the field of view 22 of the second radiometer 20 are directed respectively toward proximate portions 312 and 322 of the surface 310. In the scenario of FIG. 3, sub-surface irregularities are not present. Thus, after the structure is heated, heat flows generally uniformly through the structure and the temperatures of the proximate portions 312 and 322 are determined by the inspection device 5 to be essentially the same. Thus, a non-alert signal is emitted by the second indicator 64 in FIG. 3.

In FIG. 4, however, the inspection device is disposed near the surface 410 of a structure 400 that contains a sub-surface irregularity 402. The field of view 12 of the first radiometer 10 and the field of view 22 of the second radiometer 20 are directed respectively toward proximate portions 412 and 422 of the surface 410. The first and second radiometers 10 and 20 responsively generate signals indicative of the respective temperatures of the surface portions 412 and 422. The first radiometer 10 in FIG. 4 is disposed above a fault-free area of the structure. The second radiometer 20, however, is disposed closer to a sub-surface irregularity 402. The irregularity 402 can represent a disbanded area between adjacent layers in the structure 400, or any other localized sub-surface feature that disrupts uniform heat flow though the structure. Thus, in this scenario, subsequent to heating of the structure, the proximate portions 412 and 422 of the surface 410 exhibit different temperatures and the inspection device 5 responsively emits an alert signal through the first indicator 62 to alert an operator of the presence of the sub-surface irregularity 402.

The temperatures of the surface portions 412 and 422 in the inspection scenario of FIG. 4 are shown in the temperature-curve chart 500 in FIG. 5. It should be understood that FIG. 5 represents a simulated scenario and simulated temperature curves that are provided to convey an understanding of at least one embodiment of the disclosure. The simulated inspection scenario is initiated at time 502 by the actuation of the trigger 42 (FIG. 4). The solid curve 504 represents the time-varying temperature of the surface portion 412 and the dashed curve 506 represents the time-varying temperature of the surface portion 422 as measured respectively by the first and second radiometers 10 and 20. It is assumed that the surface 410 (FIG. 4) of the structure 400 has been already heated at a time closely preceding the time 502. Upon actuation of the trigger 42 at time 502, the temperatures of the surface portions 412 and 422 are essentially the same or effects on the device 5 otherwise are nulled by the sample and hold circuit 40. However, as the structure cools, their temperatures differ substantially in an early phase of the cooling and then ultimately equilibrate. In particular, the sub-surface irregularity 402 causes heat to be trapped along the surface portion 422. Thus, subsequent to the time 502, the temperature curve 506 corresponding to the surface portion 422 is elevated relative to the temperature curve 504, which corresponds to the surface portion 412 that cools more quickly than the surface portion 422. As the difference between the two temperature curves exceeds the threshold 54 established by the adjustment device 52, the first indicator 62 is activated to alert an operator to the likely presence of an irregularity. Thus, the first indicator 62 is activated at the time 508 when the temperature curves first depart by more than the threshold 54. The first indicator 62 remains activated until the temperature curves differ by less than the threshold 54 at the time 510 as the structure cools and the temperatures of the surface portions 412 and 422 ultimately equilibrate.

It should be understood that the device 5 may not be stationary for long during a typical inspection session. That is, FIG. 4 may represent a moment in time as the device is passed temporarily through the disposition illustrated in FIG. 4 within the time interval defined between the times 508 and 510 of FIG. 5. In such conditions, the first indicator 62 is temporarily activated to alert the operator and may be accompanied by an audible alarm from the audible signal emitter 66.

Because the temperatures of surface portions of a structure are likely to equilibrate in time, the operator of the device 5 will typically apply heat periodically to induce the temperature gradients by which sub-surface irregularities may be detected. For example, ten to twenty seconds may typically pass between the heating of a structure and temperature-equilibration among proximate surface portions despite any presence of irregularities. Thus the operator of the device 5 should be mindful of typical equilibration times for any given inspected structure and heat application technique so as not to take confidence in the activation of the second indicator 64 when the device is disposed over un-heated or temperature-equilibrated surface portions.

In at least one example, a heat device provides a shut-down function to assure that inspections provide indicator results only as the device is disposed over a recently heated surface. For example, in FIG. 5, a time interval 512 is defined between the time 502 of the actuation of the trigger 42 (FIG. 4) and the time 514 when the temperature curve 504 drops by a predefined decrement 516. In this example, upon actuation of a trigger, an inspection device monitors the signal of one of two radiometers and deactivates when the temperature represented by the monitored radiometer falls by the predefined decrement 516. This prevents a non-alert signal from being emitted after temperature equilibration of an inspected surface.

FIG. 6 is a flow chart corresponding to a method, according to at least one embodiment of the disclosure, of inspecting an aircraft structure that may be constructed of multiple layers of composite material. The depicted method 600 initiates at step 610 wherein an aircraft is visually inspected, for example, prior to a scheduled flight. In step 620, an impact site is identified. For example, a surface marking, dent, or scratch may come to the attention of a pre-flight inspector. At this stage in the method, the inspector may not be able to visibly determine whether other irregularities are present. A decision should be made as to whether the aircraft is fit for flying service. In step 630, the inspector disposes a pair of thermal radiometers near the impact site. For example, the inspector might dispose the inspection device 5 (FIGS. 3-4) near the impact site. In step 640, the outward surface of the skin of the aircraft, in the vicinity of the impact site, is heated. For example, the energy source 70 might be activated to briefly and uniformly bathe the surface with radiant thermal energy to cause heat to flow into the structure. In step 650, a determination is made as to whether a temperature difference is present by concurrently measuring the respective temperatures of proximate portions of the heated surface using a pair of thermal radiometers. For example, an operator might view the first and second indicators 62 and 64 in making this determination. The method 600 continues in view of the determination of step 650. If the temperatures are essentially the same, the aircraft is returned to flying service in step 660. If the temperatures are substantially different, further inspections are performed in step 670 and the flight of the aircraft is likely delayed or even cancelled. In performing further inspections, an operator may summon NDI specialists who may utilize additional inspection devices and methods.

A branch 680 is shown in FIG. 6 to illustrate optional additional iterations of steps 630 through 650. That is, in at least one embodiment of the method 600, the radiometers are disposed in multiple locations near the impact site. For example, the radiometers might be moved among multiple locations that surround the impact site. At any such location, a determination that a temperature difference is present in step 650 leads to step 670 where further inspections are performed. On the other hand, multiple locations surrounding the impact site may be visited without a substantial temperature difference being observed at any of the locations. In that situation, the aircraft is returned to flying service. The additional optional iterations represented by branch 680 may be particularly advantageous in inspecting an aircraft component constructed of multiple layers of composite materials. Irregularities may be detected by conducting inspections at surface portions surrounding an impact site.

As respectively shown in FIGS. 3-4, non-alert and alert signals are emitted and can be interpreted by an operator without extensive thermography training. Such an operator may use the inspection device 5 to determine whether a scratched or marked aircraft structure is ready to fly or whether extensive inspections by specialized personnel and equipment are needed. The inspection device 5 includes relatively low cost non-imaging thermal radiometers and represents a low-cost NDI device for rapid screening of markings on aircraft-component skins to determine whether sub-surface irregularities are present. The inspection device 5 can be feasibly widely distributed at aviation facilities, and can be used to make rapid fly versus no-fly decisions.

Many modifications and other embodiments of the disclosure set forth herein will come to mind to one skilled in the art to which the disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of non-destructive inspection (NDI) of a structure, the method comprising:
   identifying an irregularity on a surface of the structure;
   determining a null value representing a difference between respective response functions of a first non-imaging thermal sensor and a second non-imaging thermal sensor;
   measuring the temperature of a first portion of a surface of a structure proximate the irregularity with the first non-imaging thermal sensor;
   measuring the temperature of a second portion of the surface of the structure proximate the irregularity with the second non-imaging thermal sensor, wherein measuring the temperatures of the first and second portions each comprise halting measurement of the temperature of the respective portion once the temperature that is measured has fallen by a predefined decrement;
   determining a normalized difference signal by determining a difference signal representing any difference in temperature between the first and second portions as measured by the first and second non-imaging thermal sensors, respectively, and defining the normalized difference signal to represent any departure of the difference signal from the null value;
   repeatedly measuring different first and second portions of the surface of the structure proximate the irregularity and repeatedly determining the normalized difference signal for each of the different first and second portions of the surface of the structure that are measured; and
   emitting an alert signal based upon the normalized difference signal if the temperature of the first portion is different from the temperature of the second portion by at least a temperature difference threshold for any of the different first and second portions of the surface of the structure that are measured.

2. The method of claim 1, wherein the first thermal sensor comprises a first thermal radiometer having a first field of view, wherein measuring the temperature of the first portion of the surface of the structure comprises directing the first field of view onto the first portion, wherein the second thermal sensor comprises a second thermal radiometer having a second field of view, wherein measuring the temperature of the second portion of the surface of the structure comprises directing the second field of view onto the second portion.

3. The method of claim 2, further comprising:
receiving through the first thermal radiometer a first infrared emission from the first portion of the surface;
generating a first signal by the first thermal radiometer, the first signal indicative of the first temperature; and,
receiving through the second thermal radiometer a second infrared emission from the second portion of the surface;
generating a second signal by the second thermal radiometer, the second signal indicative of the second temperature.

4. The method of claim 1, wherein emitting an alert signal comprises emitting a light signal.

5. The method of claim 1, further comprising emitting a non-alert signal if the first temperature does not differ from the second temperature by at least the temperature difference threshold.

6. The method of claim 5, wherein emitting an alert signal comprises emitting a first light signal having a first color, and wherein emitting a non-alert signal comprises emitting a second light signal having a second color that is different from the first color.

7. The method of claim 1, further comprising heating an area of the surface, the area including the first and second portions.

8. The method of claim 1 further comprising controlling a sensitivity with which the NDI is conducted by adjustably establishing the temperature difference threshold.

9. An inspection device comprising:
a first non-imaging radiometer having a first field of view along a first axis, the first radiometer capable of generating a first signal indicative of the temperature of a first surface when the first surface is disposed in the first field of view;
a second non-imaging radiometer disposed proximate the first radiometer and having a second field of view along a second axis, the second axis different from the first axis, the second radiometer capable of generating a second signal indicative of the temperature of a second surface when the second surface is disposed in the second field of view;
an indicator element;
a comparator disposed in electronic communication with the first radiometer, the second radiometer, and the indicator element, the comparator capable of determining a difference between the first signal and the second signal;
a circuit for determining a null value representing a difference between respective response functions of the first and second non-imaging thermal sensors and for determining a normalized difference signal based upon any departure of the difference between the first and second signals from the null value and causing the indicator element to indicate, based upon the normalized difference signal, whether the temperature indicated by the first signal is different from the temperature indicated by the second signal by at least a temperature difference threshold;
a level adjust device configured to control a sensitivity of the inspection device by adjustably establishing the temperature difference threshold; and
a shut-down function configured to halt measurement of the temperature of the respective portion of the surface of the structure once the temperature that is measured has fallen by a predefined decrement.

10. The inspection device of claim 9, wherein the indicator element comprises an first indicator and a second indicator, wherein the comparator is capable of causing the first indicator to indicate when the temperature indicated by the first signal is different from the temperature indicated by the second signal by at least the temperature difference threshold, and wherein the comparator is capable of causing the second indicator to indicate when the temperature indicated by the first signal is not different from the temperature indicated by the second signal by at least the temperature difference threshold.

11. The inspection device of claim 10, wherein the first indicator comprises a first light emitter, and wherein the second indicator comprises a second light emitter.

12. The inspection device of claim 9, wherein the first radiometer consists of a non-imaging radiometer sensitive to infrared electromagnetic radiation.

13. The inspection device of claim 11, further comprising a housing connected to the first radiometer and the second radiometer; the housing maintaining the disposition of the first radiometer relative to the second radiometer such that the first axis is maintained as different from the second axis.

14. The inspection device of claim 13, further comprising a heat source connected to the housing, the heat source operable to heat a surface when the surface is disposed in the first field of view.

15. The inspection device of claim 13, further comprising an energy source connected to the housing, the energy source operable to cause heating of a structure.

16. A method of inspecting the skin of a structure below the surface of the skin, the method comprising:
determining a null value representing a difference between respective response functions of a pair of infrared radiometers;
heating the skin of the structure through an outward surface of the skin to cause heating of the surface;
concurrently measuring the respective temperatures of proximate portions of the heated surface using the pair of infrared radiometers and halting measurement of the temperature of the respective portion once the temperature that is measured has fallen by a predefined decrement;
comparing the measured temperatures to determine a normalized difference signal by determining a difference signal representing any difference in temperature between the proximate portions of the heated surface as measured by the pair of radiometers and defining the normalized difference signal to represent any departure of the difference signal from the null value;
determining the presence of an irregularity within the skin below the surface based upon the normalized difference signal if the respective temperatures of the proximate portions differ by at least a temperature difference threshold; and
controlling a sensitivity with which an inspection is conducted by adjustably establishing the temperature difference threshold.

17. The method of claim 16, wherein measuring the respective temperatures of the proximate portions of the heated surface using a pair of infrared radiometers comprises directing the field of view of a first infrared radiometer onto a first portion of the heated surface, and directing the field of view of a second infrared radiometer onto a second portion of the heated surface, the second portion proximate the first portion.

18. The method of claim 16, wherein heating a skin of a structure through an outward surface of the skin comprises directing thermal energy onto the surface.

19. A method of inspecting a layered composite aircraft structure, the method comprising:
   determining a null value representing a difference between respective response functions of a pair of thermal radiometers;
   heating a surface of a layered composite aircraft structure;
   determining whether a temperature difference is present by concurrently measuring the respective temperatures of proximate portions of the heated surface using the pair of thermal radiometers, wherein concurrently measuring the respective temperatures of proximate portions of the heated surface comprises halting measurement of the temperature of the respective portion once the temperature that is measured has fallen by a predefined decrement;
   determining a normalized difference signal by determining a difference signal representing the temperature difference and defining the normalized difference signal to represent any departure of the difference signal from the null value;
   returning the aircraft structure to flying service based upon the normalized difference signal if the temperatures differ by less than the temperature difference threshold; and
   performing further inspection of the layered composite aircraft structure based upon the normalized difference signal if the temperatures differ by at least the temperature difference threshold.

20. The method of claim 19, further comprising:
   visually inspecting the surface;
   identifying an impact site along the surface; and
   disposing the pair of thermal radiometers near the impact site.

21. The method of claim 19, further comprising:
   disposing the pair of thermal radiometers at multiple locations near the impact site and
   determining whether temperature differences are present at each of the multiple locations.

22. The method of claim 19 wherein heating a surface of an aircraft structure comprises heating multiple layers of composite material.

23. The method of claim 19 further comprising controlling a sensitivity with which an inspection is conducted by adjustably establishing the temperature difference threshold.

* * * * *